United States Patent [19]
Ohta et al.
[11] Patent Number: 4,464,290
[45] Date of Patent: Aug. 7, 1984

[54] HYPO-ALLERGENIC JASMINE OIL PROCESS FOR PRODUCING THE SAME AND COMPOSITION CONTAINING THE SAME

[75] Inventors: Saburo Ohta, Tokyo; Shoji Nakamura, Yokohama; Katsutake Hayashi, Tokyo; Katsuyuki Yomogida, Sagamihara; Hideo Morohoshi, Yokohama; Seiichi Hirose, Yokohama; Keiichi Uehara, Yokohama; Masanori Aizawa, Yokohama; Yoshihisa Sato, Yokohama; Hideyuki Ichikawa, Matsumoto; Masayuki Tejima, Tokyo; Seisaku Togano, Chigasaki, all of Japan

[73] Assignee: Shiseido Company Ltd., Tokyo, Japan

[21] Appl. No.: 360,290

[22] Filed: Mar. 22, 1982

[51] Int. Cl.$^3$ .......................... A61K 7/46; C11B 9/00
[52] U.S. Cl. .............................................. 252/522 R
[58] Field of Search ................................... 252/522 R

[56] References Cited

U.S. PATENT DOCUMENTS

| | | | |
|---|---|---|---|
| 658,846 | 2/1900 | Hesse | 252/522 R |
| 2,582,743 | 1/1952 | Bollmann et al. | 252/522 R X |
| 2,976,321 | 3/1961 | Dorsky et al. | 252/522 R X |
| 3,150,050 | 9/1964 | Safrin et al. | 252/522 R |
| 3,548,006 | 12/1970 | Scriabine | 252/522 R |
| 3,839,233 | 10/1974 | Wight et al. | 252/522 R |
| 4,308,179 | 12/1981 | Celli | 252/522 R |

FOREIGN PATENT DOCUMENTS

| | | | |
|---|---|---|---|
| 850653 | 8/1981 | U.S.S.R. | 252/522 R |

OTHER PUBLICATIONS

Chemical Abstracts 77,31741m (1972).
Chemical Abstracts 88,65874z (1978).
Drug & Cosmetic Industry V97(4), p. 580 (1965).
Manufacturing Chemist V33, p. 515 (1962).
La Parfumerie Moderne, 43:22, pp. 84-90 (1951).
Appell, American Perfumer and Cosmetics, vol. 79, pp. 25 to 39, 1964.

*Primary Examiner*—Helen M. S. Sneed
*Attorney, Agent, or Firm*—Sprung, Horn, Kramer & Woods

[57] ABSTRACT

Hypo-allergenic jasmine oil is presented. This hypo-allergenic jasmine oil can be obtained by removing coniferyl benzoate and coniferyl acetate from natural flower essential jasmine oil by means of distillation, molecular distillation, preparative gas chromatography, preparative column chromatography, alkaline treatment or any combination thereof.

4 Claims, 14 Drawing Figures

$^1$H-NMR SPECTRUM OF E $^{13}C$ – NMR SPECTRUM OF E

HYPO-ALLERGENIC JASMINE OIL PROCESS FOR PRODUCING THE SAME AND COMPOSITION CONTAINING THE SAME

The present invention relates to a hypo-allergenic jasmine oil, a process for producing the same, and a composition containing the same.

As is well-known in the perfumery, jasmine oil is an extremely important flower essential oil which is indispensable for the formulation of cosmetics, especially, for example, perfume and eau de cologne.

However, recently, it has been reported in, for example, Hideo Nakayama: Perfume Allergy and Cosmetic Contact Dermatitis. The Japanese Journal of Dermatology 84, 659–667 (1974); H. Nakayama, H. Hanaoka, and A. Ohshiro: Allergen Controlled System (ACS), page 19 published from Kanehara Shuppan, Japan (1974); W. G. Larsen: Dermatitis due to a Perfume, Contact Dermatitis, 1, 142–145 (1975); and H. Ueda and R. Hayakawa: Perfume Patch Test, The Skin Research (Japan) 20, 195–199 (1978) that jasmine oil is positive to cosmetic contact dermatitis and the allergenicity (or allergic potential) thereof becomes a problem.

The present inventors conducted allergenicity test with respect to five kinds of commercially available natural jasmine oils (i.e. samples 1 to 5). The results are shown in Table 1 below. As is clear from the results shown in Table 1 below, all the samples have allergenicity and cause cross-reactions with one another in tests using guinea pigs.

TABLE 1

| Sample challenged on animal | Challenge concentration (%) | Sample induced to animal: Sample 1 | Sample 2 | Sample 3 | Sample 4 | Sample 5 | Control | Allergenicity |
|---|---|---|---|---|---|---|---|---|
| Sample 1 | 10 | 10/10 (3.8) | 10/10 (1.3) | 10/10 (1.3) | 9/10 (1.1) | 10/10 (2.4) | 1/10 (0.1) | Yes |
| Sample 2 | 10 | 10/10 (1.3) | 10/10 (3.2) | 10/10 (2.6) | 10/10 (3.0) | 10/10 (3.9) | 0/10 (0) | " |
| Sample 3 | 10 | 10/10 (1.3) | 10/10 (1.8) | 10/10 (2.7) | 10/10 (2.6) | 10/10 (3.1) | 0/10 (0) | " |
| Sample 4 | 10 | 10/10 (1.3) | 10/10 (1.8) | 10/10 (2.1) | 10/10 (2.4) | 10/10 (2.2) | 0/10 (0) | " |
| Sample 5 | 10 | 10/10 (1.0) | 10/10 (1.7) | 10/10 (1.9) | 10/10 (1.2) | 10/10 (2.6) | 0/10 (0) | " |

*1 The results are shown in "Number of positively reacted animals/Number of animals tested (Average score of allergenic reaction)".

The allergenicity test was carried out as follows.

Healthy Hartley strain albino guinea pigs weighing between 380 g and 450 g were used as a group of test animals. The test was carried out according to a Magunusson and Kligman's GPMT method (Guinea pig maximization test, 1970 Allergic Contact Dermatitis in the Guinea Pig, Spring Field, Ill., C. C. Thomas).

The inducing (or sensitizing) treatment was as follows. That is, the following three liquors (i), (ii) and (iii) were prepared.

Liquor (i): an emulsion obtained by emulsifying Freund's Complete Adjuvant (available from Difco Co., Ltd., it is abbreviated as "FCA" hereinbelow for the brevity's sake) with an equal amount of water.

Liquor (ii): 10 (W/W) % FCA solution of test sample

Liquor (iii): 10 (W/W) % emulsion of the test sample which emulsion was prepared by emulsifying 20 (W/W) % FCA solution of the sample with an equal amount of water to be tested.

The shoulder region of the guinea pigs was clipped and shaved and 0.1 ml each of the liquors (i), (ii) and (iii) were injected intradermally in this order at the left and right depilated nuchal skins symmetrically apart from the back center line. The injected points were six in total. After 6 days from the intradermal injection, the injected portions were shaved and 0.2 g of 10 (W/W) % sodium lauryl sulfate in white petrolatum was applied to each injected portion. After 1 day, a closed patch test was conducted by applying 0.2 ml of the liquor (ii) to each nuchal skin for 48 hours. Then, the closed patch was removed and the inducing treatment was completed.

After 21 days from the intradermal injection, approximately 10 microliters of the test sample solutions in acetone having the challenge concentrations listed in Table 1 were applied topically to the flank skin of the sensitized quinea pigs (i.e. challenge test).

As a control, ten guinea pigs, in which only the liquor (i) was intradermally injected during the sensitizing treatment, were used and the challenge test was carried out in the same manner as described above. Thus, the non-specific skin irritation reaction of the test sample was distinguished. The results were examined after 24 and 48 hours from the application. The observation or evaluation was based on the following scoring criteria.

| | Score |
|---|---|
| (1) Formation of Erythema | |
| no erythema | 0 |
| very slight erythema | 1 |
| well defined erythema | 2 |
| moderate to strong erythema | 3 |
| severe strong erythema to slight eschar formation | 4 |
| (2) Formation of Edema | |
| no edema | 0 |
| very slight edema | 1 |
| slight edema | 2 |
| moderate edema | 3 |

$$\text{Fractional Response} = \frac{\text{Number of positively reacted animals}}{\text{Number of animals tested}},$$

$$\text{Average score} = \frac{\Sigma\ (\text{Score of erythema} + \text{Score of edema})}{\text{Number of animals tested}}$$

Accordingly, objects of the present invention are to eliminate the above-mentioned problem of the natural jasmine oil and to provide hypo-allergenic jasmine oil.

Another object of the present invention is to provide a process for producing hypo-allergenic jasmine oil.

Further object of the present invention is to provide a composition containing hypo-allergenic jasmine oil.

Other objects and advantages of the present invention will be apparent from the following description.

In accordance with the present invention, there is provided hypo-allergenic jasmine oil in which coniferyl benzoate and coniferyl acetate are substantially removed. This jasmine oil contains no substantial amount of substances having a count number of 47.5 through 49.5 determined by a gel permeation chromatography under the conditions listed in Table 5 below.

In accordance with the present invention, there is also provided a process for producing hypo-allergenic jasmine oil in which coniferyl benzoate and coniferyl acetate are substantially removed from natural flower essential jasmine oil by distillation, molecular distillation, preparative gas chromatography, preparative column chromatography, alkaline treatment or any combination thereof.

In accordance with the present invention, there is further provided a hypo-allergenic jasmine composition comprising (i) hypo-allergenic jasmine oil in which coniferyl benzoate and coniferyl acetate are substantially removed and (ii) a perfume controlling agent.

The present invention will be better understood from the description set forth below with reference to the accompanying drawings in which.

Figure 1:
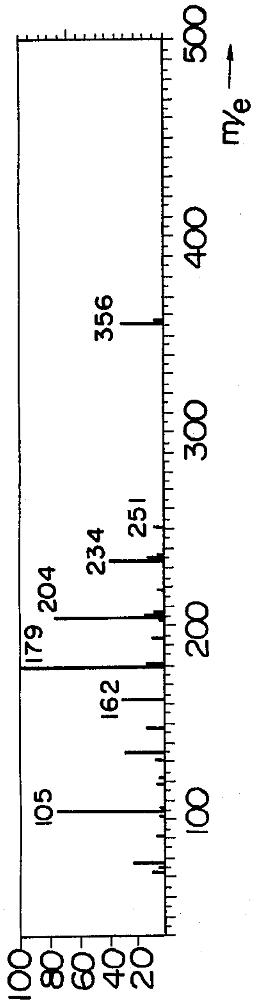
FIG. 1 is a MS spectrum of TMS (trimethyl silyl) derivative of spot E.
Figure 2:
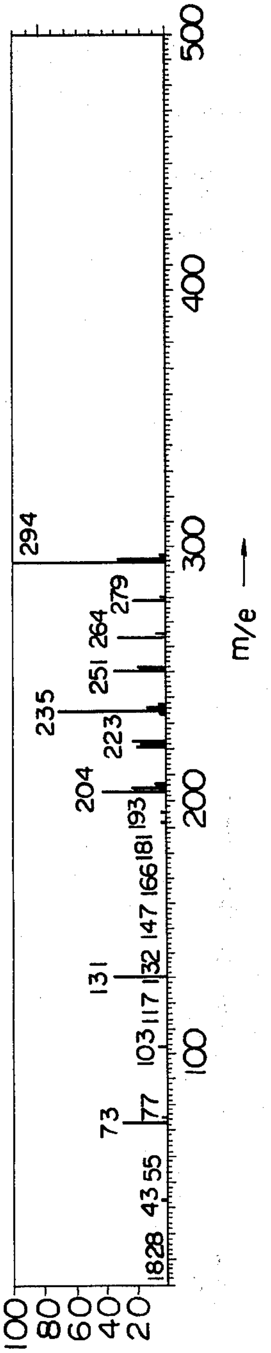
FIG. 2 is a MS spectrum of TMS derivative of spot F.
Figure 3:
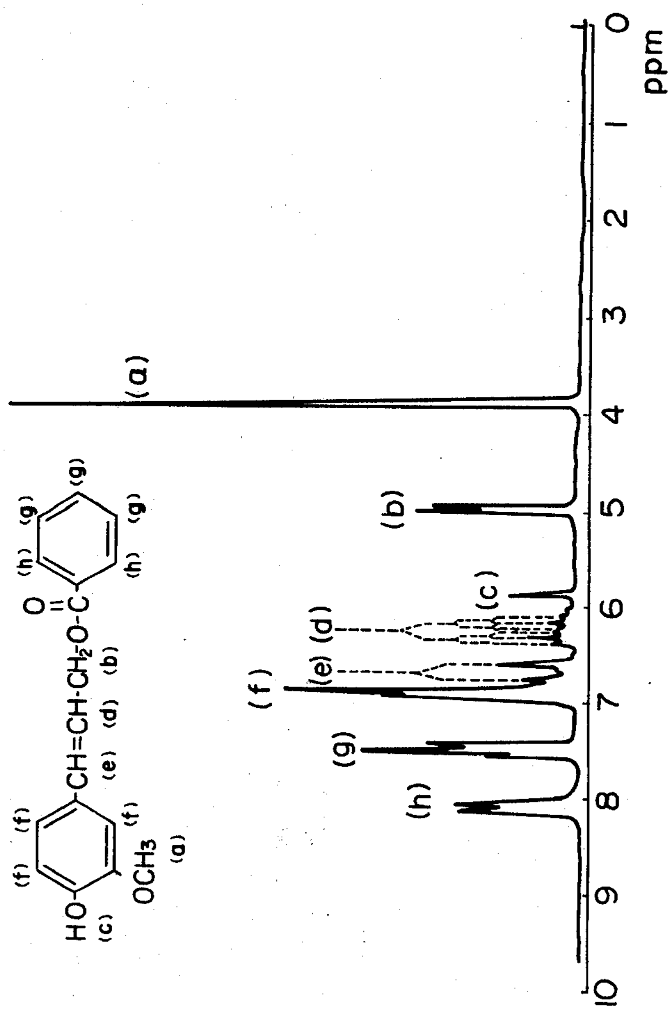
FIG. 3 is a $^{1}H$-NMR spectrum of spot E.
Figure 4:
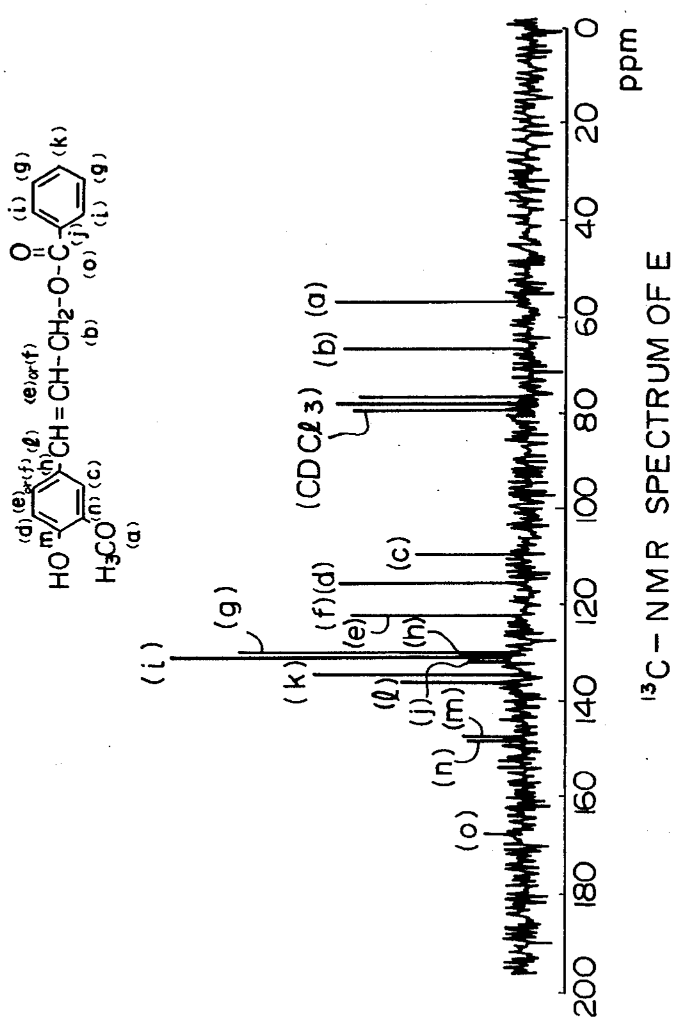
FIG. 4 is a $^{13}C$-NMR spectrum of spot E.

The present inventors have first found the allergenic substances contained in natural jasmine oil. We have isolated these allergenic substances and identified the structures thereof. According to the present invention, these allergenic substances can be removed from jasmine oil without denaturing the jasmine oil to produce hypo-allergenic jasmine oil. We believe that this is epoch-making and very worthwhile from the industrial point of view.

The identification of the allergenic substances will now be described.

Five hundreds and ten grams of natural jasmine oil was distilled to separate into 161 g of a distillate fraction up to 94° C./0.5 mmHg and 347 g of the residue. Although the distillate fraction did not exhibit allergic reaction, the distillation residue exhibited strong allergenicity.

Three hundreds and twenty-eight grams of the distillation residue was subjected to a molecular distillation under the conditions listed in Table 2 below. A centrifugal type molecular distillation apparatus CMS-5A (manufactured by Bendix Co.) was used. The allergenicity test results are also shown in Table 2 below.

TABLE 2

| Fraction | Pressure ($\times 10^{-3}$ mmHg) | Temperature (°C.) | Yield (g) | Foreign odor | Induction test concentration (%) | Sensitized animal group | Control animal group | Allergenicity |
|---|---|---|---|---|---|---|---|---|
| 1 | 5.5-12 | -70 | 15.31 | None | | | | |
| 2 | 5.1-5.5 | 70-71 | 16.66 | " | | | | |
| 3 | 4.9-5.1 | 71-75 | 21.16 | " | 1.5 | 4/10 (0.4) | 0/10 | No |
| 4 | 3.8-4.9 | 75-80 | 16.67 | " | | | | |
| 5 | 3.4-3.8 | 80-80 | 17.46 | " | | | | |
| 6 | 3.1-3.4 | 80-81 | 16.08 | " | | | | |
| 7 | 3.0-3.1 | 81-85 | 14.72 | " | | | | |
| 8 | 2.9-3.0 | 85-90 | 15.85 | " | 2% | 10/10 (2.8) | 0/10 | Yes |
| 9 | 2.9 | 90-95 | 16.88 | " | | | | |
| 10 | 2.8-2.9 | 95-105 | 11.43 | " | | | | |
| 11 | 2.8 | 105-110 | 11.98 | " | | | | |
| Residue | — | — | 139.68 | " | 3% | 10/10 (2.5) | 0/10 | Yes |
| Trap | — | — | 12.45 | " | | | | |

As is clear from the results shown in Table 2 above, the fractions 5 through 11 have strong allergenicity. Thus, the allergenic substances were mainly present in these fractions.

The fractions 5 through 11 were fractionated under the operation conditions listed in Table 3 below by means of a countercurrent type partition chromatography method.

TABLE 3

| | |
|---|---|
| Apparatus: | a rotary type multi-stage countercurrent chromatograph Model RLCC (manufactured from Tokyo Rika kiki Co. in Japan) |
| Separation tube: | 11 mm i.d. × 900 mm × 8 tubes |
| Solvent: | n-pentane (mobile phase)/90% (V/V) aqueous methanol (stationary phase) |
| Flow rate: | 0.5 ml/min |
| Rotation number: | 20 rpm |
| Sample size: | 0.1-3 g |
| Detector: | UV detector (280 nm) |

While monitoring at 280 nm by means of a UV detector, the fractions by which benzyl benzoate were completely fractionated were concentrated as a pentane portion, and the fractions thereafter were combined with a 90% (V/V) aqueous methanol layer and concentrated as a water-methanol portion. As a result, 27 g of the pentane portion and 3 g of the water-methanol portion were obtained. The allergenicity tests were carried out. The results are shown in Table 4 below.

TABLE 4

| Challenge sample | Challenge concentration % in acetone | Sensitized animal group | Control animal group | Allergenicity |
|---|---|---|---|---|
| Molecular distillation fractions 5-11 | 5 | 10/10 (2.8) | 0/10 | Yes |
| Water-methanol portion | 0.5 | 10/10 (1.6) | 0/10 | Yes |
| Pentane portion | 4.5 | 0/10 | 0/10 | No |
| Water-methanol portion + pentane portion | 5 | 10/10 (2.9) | 0/10 | Yes |

As is clear from the results shown in Table 4 above, no allergenicity was observed in the pentane portion. Contrary to this, the water-methanol portion exhibited the allergenicity and contained the allergenic substances in the concentrated state.

Furthermore, the combined water-methanol and pentane portions had stronger allergenicity compared with the water-methanol portion alone and similar to that of fractions 5 through 11 of the molecular distillation, before separation by means of countercurrent type partition chromatography. It has been noted that the allergenicity of the water-methanol portion was strengthened by the pentane portion.

The water-methanol portion was then fractionated into three fractions, that is, fraction A having a count number of 36.5 through 47.5, fraction B having a count number of 47.5 through 51.5, and fraction C having a count number of 51.5 through 58, under the conditions listed in Table 5 below by means of a high speed liquid chromatograph. As is clear from the results shown in Table 6 below, strong allergenicity was observed in fraction B.

TABLE 5

| | |
|---|---|
| Apparatus: | High speed liquid chromatograph HLC-802UR manufactured by Toyo Soda Kogyo Co. in Japan |
| Column: | TSK GEL G 2000 $H_8$ × 4 |
| Column temperature: | 40° C. |
| Solvent: | Tetrahydrofuran |
| Sample concentration: | 0.2-2% |
| Sample size: | 100 μl |
| Flow rate: | 1.0 ml/min at 80 kg/cm$^2$ |
| Detector: | UV absorption detector (i.e. UV), 280 nm; A standard 254 nm lamp was used with a transformer (i.e. phosphor plate, photohead 280) Differential refractometer detector (i.e. RI) |

The fraction B was subjected to GPC analysis to form three large UV peaks of 47.5 through 49.5 counts (i.e. $U_1$ fraction), 49.5 through 50.5 counts (i.e. $U_2$ fraction), and 50.5 through 51.5 counts (i.e. $U_3$ fraction). Allergenicity tests of these $U_1$, $U_2$ and $U_3$ fractions were carried out after fractionation. The results are shown in Table 7 below.

As is clear from the results shown in Table 7 below, strong allergenicity was observed in the $U_1$ and $U_2$ fractions and no allergenicity was observed in the $U_3$ fraction.

TABLE 6

| Challenge sample | Challenge test concentration % in acetone | Sensitized animal group | Control animal group | Allergenicity |
|---|---|---|---|---|
| Fraction A | 0.2 | 0/10 | 0/10 | No |
| Fraction B | 0.2 | 10/10 (2.3) | 0/10 | Yes |
| Fraction C | 0.2 | 2/10 (0.2) | 0/10 | Weak |

TABLE 7

| Challenge sample | Challenge test concentration % in acetone | Sensitized animal group | Control animal group | Allergenicity |
|---|---|---|---|---|
| Fraction $U_1$ | 0.2 | 10/10 (2.2) | 0/10 | Yes |
| Fraction $U_2$ | 0.2 | 10/10 (2.6) | 0/10 | Yes |
| Fraction $U_3$ | 0.2 | 0/10 (0) | 0/10 | No |

2.5 g of the water-methanol portion was repeatedly fractionated under the conditions shown in Table 8 below to obtain a large amount of the fraction corresponding to the fractions $U_1$ and $U_2$. Thus, 40 mg of the fractions having a count number of 37.2 through 37.8 was obtained.

TABLE 8

| | |
|---|---|
| Apparatus: | Liquid Chromatograph Model LC-08 manufactured by Nippon Bunseki Kogyo Co. in Japan |
| Sample conc.: | 5-10% solution in chloroform |
| Sample size: | 1.53 ml |
| Column: | JAIGEL 2H × 1 + 3H × 1 (i.d. 2 mm × 600 mm each) |
| Solvent: | Chloroform |
| Flow rate: | 3 ml/min |
| Temp.: | Room temp. |
| Detector: | UV and RI |
| Sensitivity: | UV; × 64, RI; × 128 |
| Chart speed: | 20 cm/hr |

Forty milligrams of the above fraction were separated by means of a preparative TLC (PLC Plate Silica gel 60 available from Merck Co.; Developing solvent: chloroform). Thus, two portions having an $R_f$ value of not less than approximately 0.55 and an $R_f$ value of not more than approximately 0.35 were obtained.

The allergenicity tests of these two portions were carried out. The results are shown in Table 9 below.

As is clear from the results shown in Table 9 below, no allergenicity was observed in the portion having an $R_f$ value of not more than approximately 0.35 and it was confirmed that the allergenic substances were concentrated into the portion having an $R_f$ value of not less than approximately 0.55.

TABLE 9

| Challenge sample | Challenge test concentration % in acetone | Sensitized animal group | Control animal group | Allergenicity |
|---|---|---|---|---|
| $R_f \geqq 0.55$ | 0.2 | 10/10 (2.3) | 0/10 | Yes |
| $R_f \leqq 0.35$ | 0.2 | 0/10 | 0/10 | No |

Ten milligrams of the portion having an $R_f$ value of not less than about 0.55 were analyzed by means of a TLC (silica gel 60, 0.25 mm, available from Merck Co.;

Developing solvent: chloroform). Thus, 3 mg of a spot having an $R_f$ value of approximately 0.65 (i.e. spot E) and 5 mg of a spot having an $R_f$ value of approximately 0.55 (i.e. spot F) were separated. The spots E and F were analyzed by a gas chromatography (i.e. GC). As a result, it was observed that each spot has one peak.

FT-IR (Fourier transform infrared), GC-MS (Gas chromatograph mass), $^{1}H$-NMR (Protan nuclear magnetic resonance) and $^{13}C$-NMR (Carbon 13 nuclear magnetic resonance) spectra of spots E and F were obtained. The MS spectra of the trimethyl silyl (TMS) derivatives of the spots E and F and the $^{1}H$-NMR and $^{13}C$-NMR spectra of the spot E are illustrated in FIGS. 1 through 4.

From the analysis of the above data, it was identified that the spot E was coniferyl benzoate having the following chemical structure:

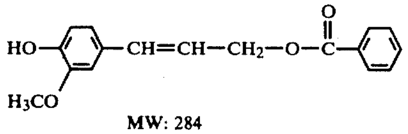 ; and

MW: 284 the spot F was coniferyl acetate having the following chemical structure;

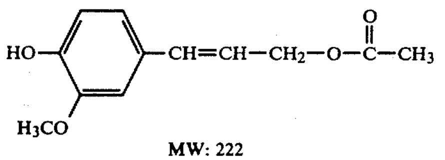

MW: 222

On the other hand, coniferyl benzoate and coniferyl acetate were synthesized. The allergenic test of these compounds were carried out on the skin of guinea pigs sensitized with natural jasmine oil. The results are shown in Table 10 below. As is clear from the results shown in Table 10 below, both compounds have strong allergenicity.

TABLE 10

| Challenge sample | Challenge test concentration % in acetone | Sensitized animal group | Control animal group | Allergenicity |
|---|---|---|---|---|
| Coniferyl benzoate | 1 | 5/5 (2.8) | 0/5 | Yes |
| Coniferyl acetate | 1 | 5/5 (2.8) | 0/5 | Yes |

Furthermore, when the synthesized coniferyl benzoate and coniferyl acetate were analyzed under the conditions shown in Table 5 above by means of GPC, coniferyl benzoate had a strong UV absorption peak at a region of 47.5–49.5 counts corresponding to the above-mentioned $U_1$ fraction (this peak is called "$U_1$ peak" hereinafter) and coniferyl acetate had a strong UV absorption peak at a region of 49.5–50.5 counts corresponding to the above-mentioned $U_2$ fraction (this peak is called "$U_2$ peak" hereinafter).

In addition, jasmine oil contains no substantial amount of substances, other than coniferyl benzoate, having the $U_1$ peak. Accordingly, the presence of coniferyl benzoate in jasmine oil can be readily determined from the UV chromatogram of GPC under the conditions shown in Table 5 above. Contrary to this, since jasmine oil contains substances, other than coniferyl acetate, having a $U_2$ peak, the presence of coniferyl acetate in jasmine oil cannot be determined only by the UV chromatogram. However, it has been found that the coniferyl acetate present in jasmine oil can be precisely determined quantitatively under the conditions listed in Table 11 below by a gas chromatograph-mass fragment graphy analysis (which is referred to as "MF method" herein).

TABLE 11

| | |
|---|---|
| GC-Mass apparatus: | Hitachi GC-Mass Model M-80 |
| Separation column: | Diasolid ZT, 80–100 mesh (i.d. 2 mm × 2 m) |
| Carrier gas: | He, 30 ml/min |
| Ionization voltage: | 20 eV |
| Sample: | Trimethyl silyl derivative of coniferyl acetate |
| Column temp.: | 150° C. |
| Selected ion: | m/e 294 |
| Retention time: | 6.0 min |

The content of coniferyl acetate in a sample can be determined from the peak height, as compared with the peak height obtained from the determination of the standard sample containing a known concentration of synthetic coniferyl acetate.

For example, the MF analysis results of natural jasmine oil (produced in Egypt) and a mixture of hypo-allergenic jasmine oil (i.e. a mixture of 32 parts of DI-1 of Example 12, 16 parts of the alkaline treated portion of Example 12 and 18 parts of the synthetic adsorbent treated portion of Example 12) are shown in Table 12 below.

TABLE 12

Figure 6:
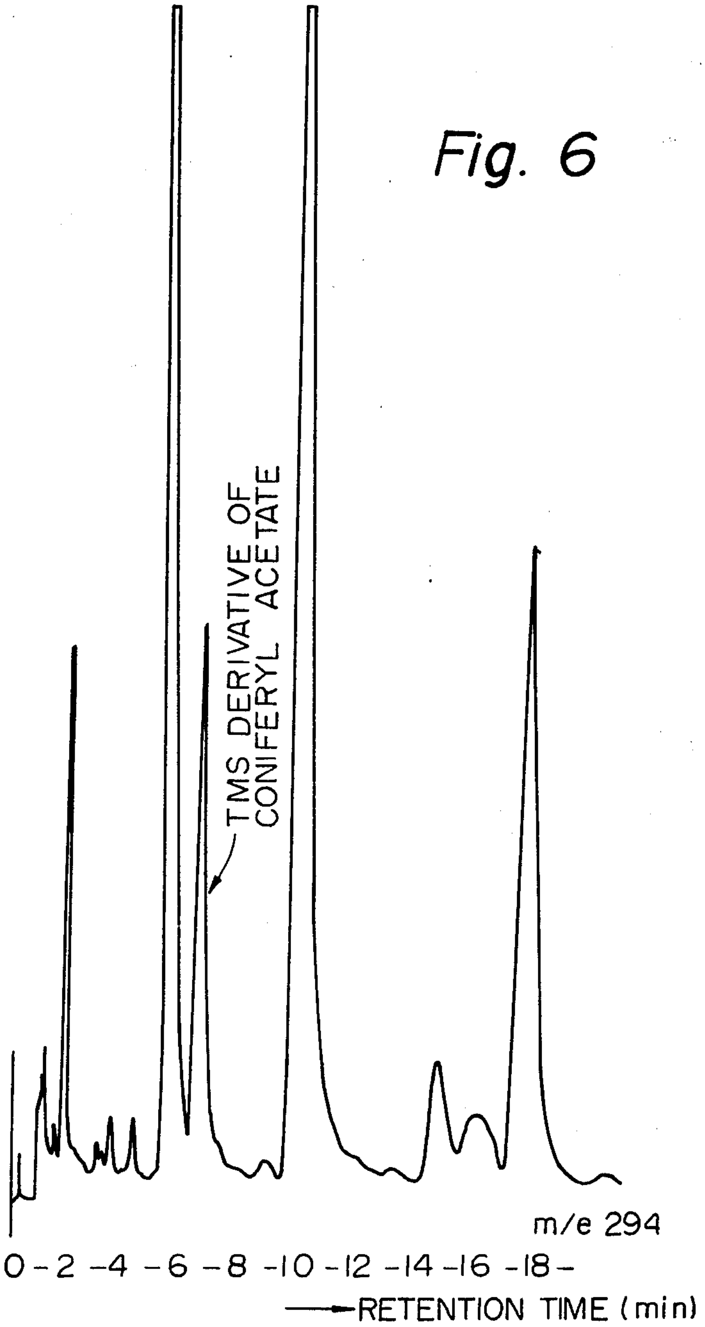
FIG. 6 is a MF chromatogram of a 1% TMS derivatives of natural jasmine oil (produced in Egypt) in hexane solution.
Figure 7:
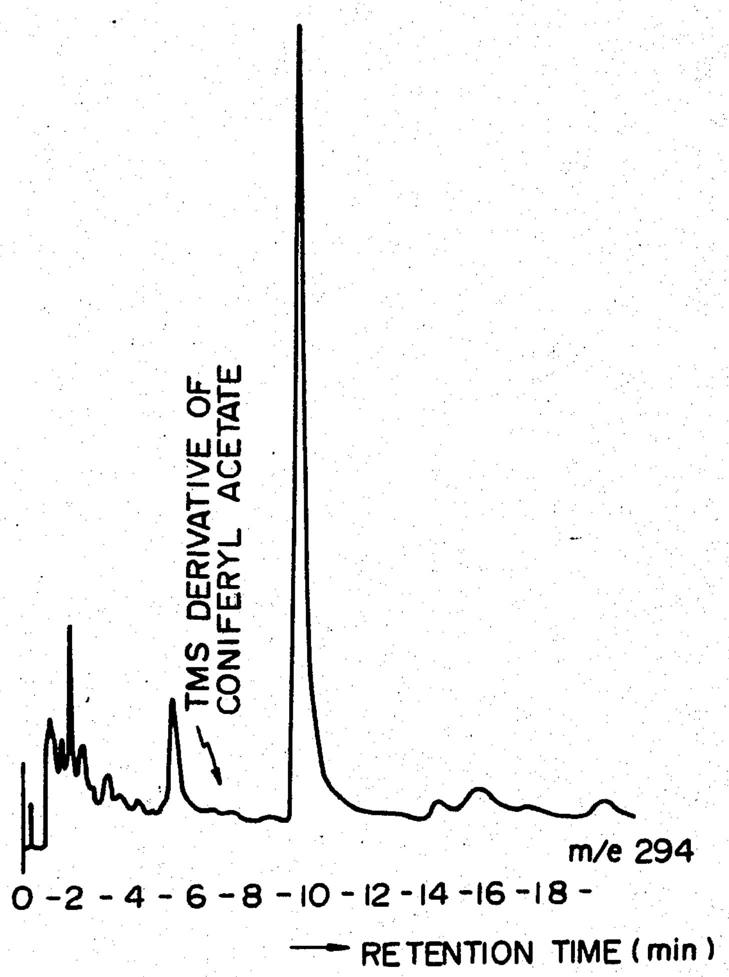
FIG. 7 is a MF chromatogram of TMS derivatives of hypo-allergenic jasmine oil (i.e. combined oil of DI-1 portion, the alkaline treated portion and the polymeric adsorbent treated portion of Example 12)

| Sample | Coniferyl acetate | Analysis data |
|---|---|---|
| Natural jasmine oil (Egypt) | 1130 ppm | See FIG. 6 |
| Mixture of hypo-allergenic jasmine oil | non detected | See FIG. 7 |

Figure 5:
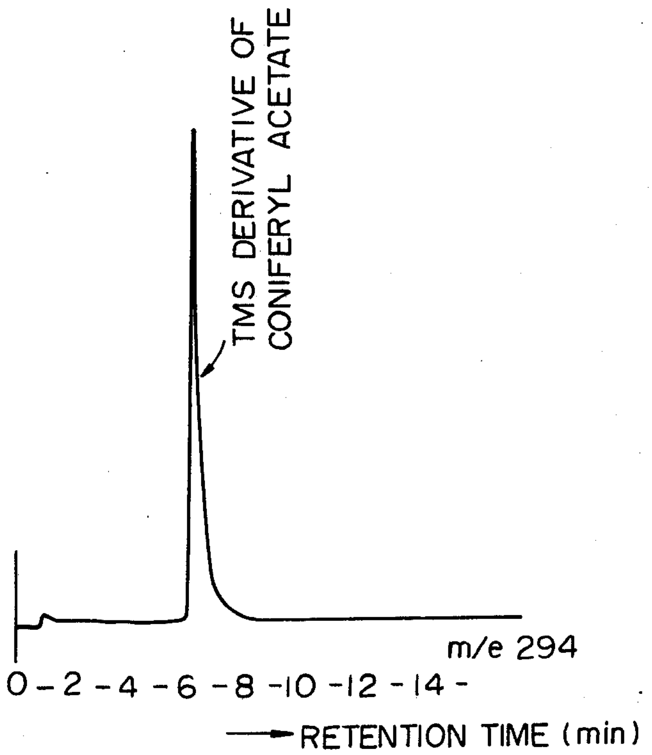
FIG. 5 is a MF chromatogram of a 10 ppm TMS derivative of synthetic coniferyl acetate in hexane solution.

The content of coniferyl acetate contained in the natural jasmine oil was approximately 1130 ppm from the determination based on the peak height a MF chromatogram of a synthetic coniferyl acetate solution having a known content thereof 10 ppm. FIG. 5 illustrate the MF chromatogram of the above-mentioned synthetic coniferyl acetate solution. FIG. 7 illustrates a MF chromatogram of the above-mentioned mixture of the hypo-allergic jasmine oil. When a GPC analysis was used, an interference peak having no allergenicity is present at a $U_2$ peak position (i.e. coniferyl acetate position) and, therefore, accurate determination could not be effected. Contrary to this, when a MF method was used, no interference peak was present and, therefore, it was confirmed that the amount of coniferyl acetate was remarkably decreased and the coniferyl acetate could not be detected. Furthermore, although the presence of coniferyl benzoate in the hypo-allergenic jasmine oil listed in Table 12 was analyzed, by means of a MF method, under the conditions of a column temperature of 210° C., a selected ion of m/e 179 (m/e 179 was selected because it has a large S/N ratio as compared with parent ion of m/e 356) and a retention time of 6.6 min, no coniferyl benzoate was detected.

In addition, although the molecular distillation residue has strong allergenicity as shown in Table 2 above, it was also confirmed that the molecular distillation residue contained the allergenic coniferyl benzoate and coniferyl acetate.

As discussed above, the present inventors found the main allergenic compounds contained in natural jasmine oil. The process for removing these allergenic substances from natural jasmine oil can be applied to those produced in, for example, Egypt, Grasse and Morocco.

The hypo-allergenic jasmine oil according to the present invention can be obtained from natural flower essential jasmine oil by distillation, molecular distillation, preparative gas chromatography, preparative column chromatography, alkaline treatment alone or any combination thereof.

According to the present invention, the distillation, the molecular distillation or a combination thereof is first effective for removing the allergenic substances from natural jasmine oil. Since natural jasmine oil is thermally unstable, natural jasmine oil is heretofore produced without heating. However, it has been found that the jasmine oil can be unexpectedly distilled without generating by-note derived from the decomposition.

Conventional distillation techniques such as simple distillation, rectification can be suitably used in the practice of the present invention. Furthermore, conventional molecular distillation utilizing for example, a centrifugal type, falling film type, wiper type or pot type apparatus can be suitably used.

Figure 8:
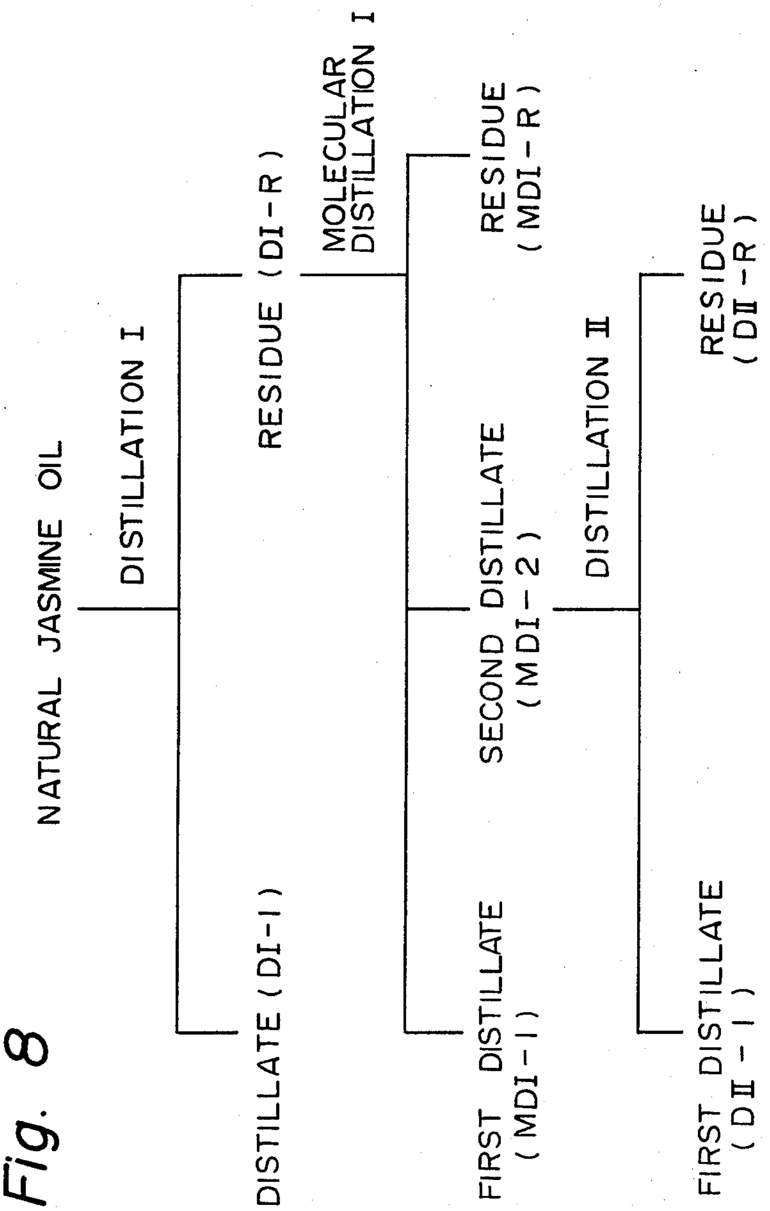
FIG. 8 is one basic flow chart of the present invention.
Figure 9:
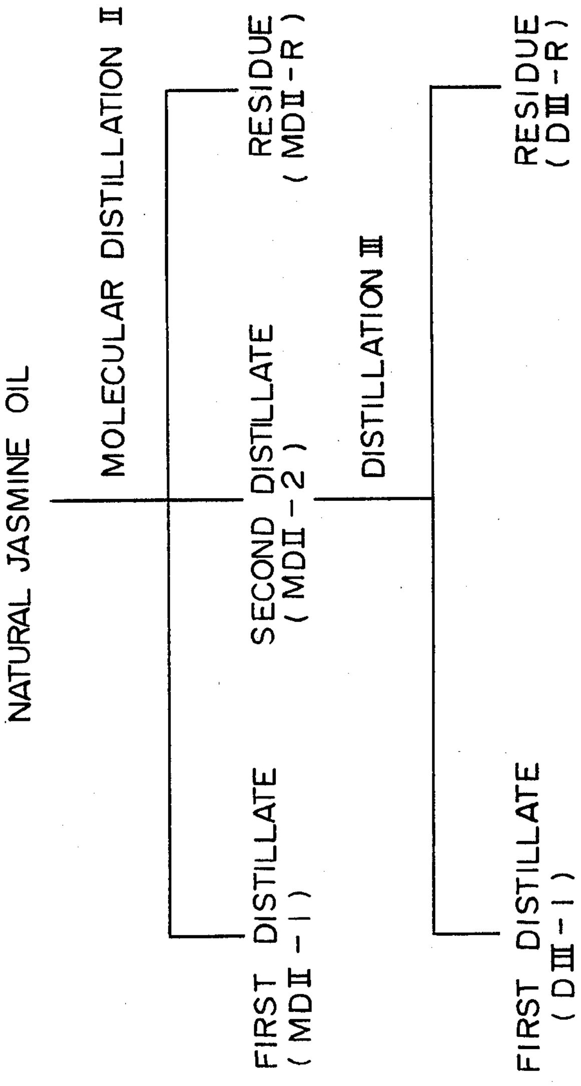
FIG. 9 is another basic flow chart of the present invention.

According to this process, hypo-allergic jasmine oil can be recovered at a maximum recover rate of 50% by weight. Referring to FIGS. 8 and 9 showing basic flow charts of the present invention, the distillation and molecular distillation methods will now be explained.

Natural jasmine oil is first distilled at a distillation I. Typical experimetal results are shown in Table 13 below. As is clear from the results shown in Table 13 below, jasmine oil having no by-note and no allergenicity is obtained by the distillation.

TABLE 13

| Experiment No. | | Conditions | Weight (%) | By-note | Allergenicity |
|---|---|---|---|---|---|
| No. | Distillate | −99° C./0.4 mm Hg | 32 | No | No |
| 1 | Residue | — | 67 | No | Yes |
| No. | Distillate | −105° C./0.4 mm Hg | 36 | No | No |
| 2 | Residue | — | 63 | No | Yes |
| No. | Distillate | −112° C./0.4 mm Hg | 40 | Yes | Yes |
| 3 | Residue | — | 59 | Yes | Yes |

In order to obtain hypo-allergenic jasmine oil, the amount of the distillate should be not more than 36 parts by weight, desirably not more than 34 parts by weight, based on 100 parts by weight of natural jasmine oil. The distillate in an amount of not more than 36 parts by weight obtained from the distillation I is called "DI-1" hereinbelow.

The residue in the distillation I (which is referred to as "DI-R" herein) may, then, be subjected to molecular distillation at a molecular distillation I. Typical experimental results are shown in Table 14 below. As is clear from the results shown in Table 14 below, the molecular distillation is desirably carried out at a temperature of not more than 110° C., since by-note is generated when the molecular distillation temperature is 130° C. or more. Hypo-allergenic jasmine oil can be obtained when the total amount of the first distillate of the molecular distillation I and DI-1 of the distillation I is not more than 45 parts by weight based on 100 parts by weight of the starting natural jasmine oil. The first distillate of the molecular distillation I, which is obtained in an amount such that the amount thereof is not more than 30 parts by weight based on 100 parts by weight of the starting natural jasmine oil and the combined amount thereof with DI-1 is not more than 45 parts by weight is referred to as "MDI-1" hereinbelow.

TABLE 14

| Distillate No. | Pressure ($\times 10^{-2}$ mmHg) | Temperature (°C.) | Weight (g) | By-note |
|---|---|---|---|---|
| 1 | 4.4 | -70 | 14.9 | No |
| 2 | 3.1–4.4 | 70–75 | 13.8 | " |
| 3 | 2.7–3.1 | 75–78 | 9.5 | " |
| 4 | 2.6–2.7 | 78–80 | 12.4 | " |
| 5 | 2.7–3.0 | 80–100 | 11.2 | " |
| 6 | 2.9–3.0 | 100–110 | 7.9 | " |
| 7 | 2.9–3.0 | 110–114 | 8.2 | " |
| 8 | 2.8–3.0 | 114–130 | 10.3 | " |
| 9 | 2.8–3.0 | 130–160 | 9.1 | Yes |
| Residue | — | — | 38.6 | " |
| Trap | — | — | 10.4 | " |

Apparatus: Centrifugal type molecular distillation apparatus CMS-5A (Bendix Co.)
Feed: DI-R 150.3 g (32% of distillate DI-1 was removed from the starting natural jasmine oil)

Furthermore, a second distillate, which is obtained from the molecular distillation I after removing the above-mentioned first distillate MDI-1 in an amount such that the total amount of DI-1, MDI-1 and the second distillate is not more than 77 parts by weight, desirably not more than 56 parts by weight, based on 100 parts by weight of the starting jasmine oil, is referred to as "MDI-2". MDI-2 thus obtained is then distilled at a second distillation II to obtain hypo-allergic distillate, the amount of which is such that the amount of this distillate is not more than 36 parts by weight based on 100 parts by weight of the starting jasmine oil and the total amount of this distillate, DI-1 and MDI-1 is not more than 45 parts by weight based on 100 parts by weight of the starting jasmine oil. This distillate is referred to as "DII-1" hereinbelow. It should be noted that the combined MDI-1 and MDI-2 derived from the molecular distillation I (this combined distillate is referred to as "distillate MDI-12") can be used, without separating, as a feed material for the distillation II. The residues of the above-mentioned molecular distillation I and distillation II are referred to as "MDI-R" and "DII-R," respectively. MDI-R and DII-R have allergenicity.

Figure 10:
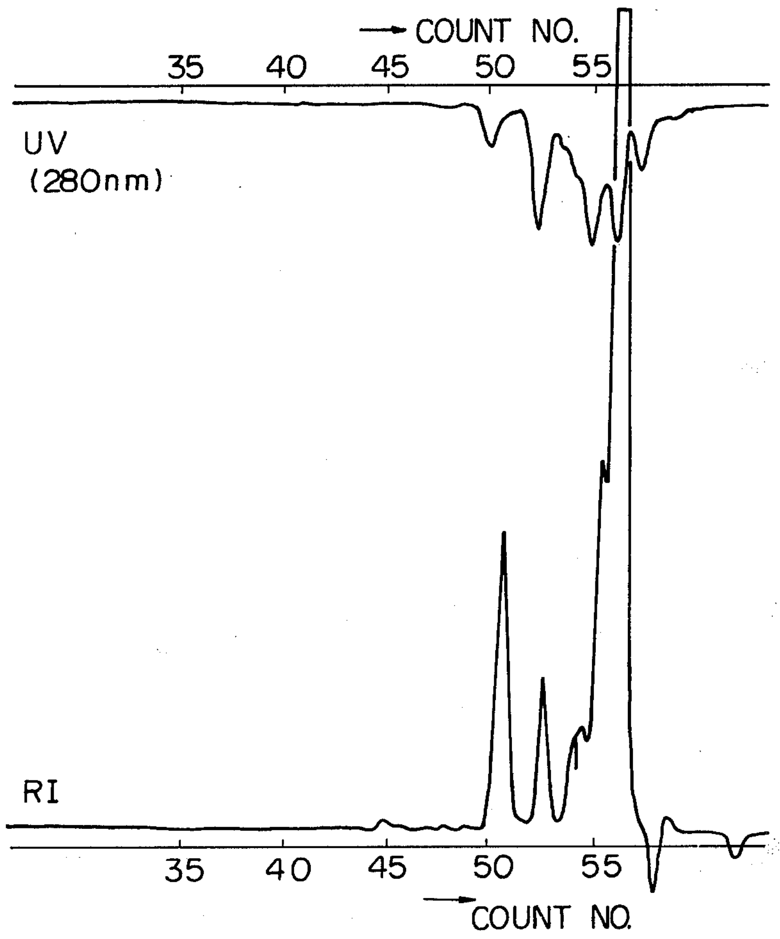
FIG. 10 is a GPC chromatogram of DI-1 portion of Example 1.

Hypo-allergenic jasmine oil can also be obtained from natural jasmine oil directly by the molecular distillation. That is, as is shown in FIG. 10, natural jasmine oil is subjected to a molecular distillation II to separate a first distillate, a second distillate and the residue. MDII-1 is defined as the first distillate, the amount of which is not more than 30 parts by weight based on 100 parts by weight of the starting jasmine oil. MDII-2 is defined as the second distillate, the amount of which is such that the total amount of MDII-1 and MDII-2 is not more than 77 parts by weight based on 100 parts by weight of the starting jasmine oil. MDII-2 is distillated at a distillation III to separate hypo-allergenic distillate. DIII-1 is defined as the distillate from the distillation III, the amount of which is such that the amount of DIII-1 is not more than 36 parts by weight based on 100 parts by weight of the starting jasmine oil and that the total amount of DIII-1 and MDII-1 is not more than 45 parts by weight. It should be also noted that MDII-1 and MDII-2 derived from the molecular distillation II can be used in combination (which is referred to as "MDII-12"), without separating, as a feed material for the distillation III. The residues of the above-mentioned molecular distillation II and distillation III are referred to as "MDII-R" and "DIII-R" respectively. MDII-R and DIII-R have allergenicity.

As explained hereinabove, according to the present invention, the allergenic substances are effectively and efficiently removed from natural jasmine oil by the above-mentioned combination of the distillation step or steps and the molecular distillation step, especially by the process in which low boiling point substances are first removed by a distillation and high boiling point substances are then separated by molecular distillation and finally the distillate derived from the molecular distillation is again distillated.

According to the present invention, hypo-allergenic jasmine oil can also be produced by an alkaline treatment (or washing) of natural jasmine oil. For example, natural jasmine oil dissolved in a water-insoluble solvent such as n-pentane, n-hexane and ethers is washed with an aqueous solution of, for example, sodium hydroxide or potassium hydroxide. Thus, hypo-allergenic jasmine oil can be obtained. This alkaline treatment can be advantageously used together with the above-mentioned distillation and/or molecular distillation. Especially, the above-mentioned portions MDI-2, MDI-12, MDII-2 and MDII-12 can be effectively subjected to the alkaline treatment, although the other portions and residues can be subjected to the alkaline treatment. Furthermore, the alkaline treatment can be applied to the below-defined distillate DII-2 which is obtained as a second distillate from MDI-2 by the distillation II, or the below-defined distillate DIII-2 which is obtained as a second distillate from MDII-2 by the distillation III. That is, DII-2 is defined as a distillate which is obtained as a second distillate from MDI-2 in such a manner that the total amount of DI-1, MDI-1, DII-1 and DII-2 is not more than 55 parts by weight based on 100 parts by weight of the starting jasmine oil. DIII-2 is defined as a distillate which is obtained as a second distillate from MDII-2 in such a manner that the total amount of MDII-1, DIII-1 and DIII-2 is not more than 55 parts by weight based on 100 parts by weight of the starting jasmine oil. In addition, the alkaline treatment can further be applied to the combined DII-1 and DII-2 derived from, without separating, the distillation II (which is referred to as "DII-12"), or the combined DIII-1 and DIII-2 derived from, without separating, the distillation III (which is referred to as "DIII-12").

According to the present invention, hypo-allergenic jasmine oil can further be effectively produced by preparative gas chromatography of natural jasmine oil. That is, the starting natural jasmine oil is introduced into a gas chromatography provided with a polar column (for example, PEG20M, FFAP). The fractions discharged from the column are introduced into a collection tube where the separated fractions are cooled to be liquefied. Thus, hypo-allergenic jasmine oil can be obtained. It is believed that the allergenic components in the natural jasmine oil are removed by thermal decomposition and/or adsorption in the column. Furthermore, especially, the portions MDI-2, MDI-12, MDII-2, DII-12 and DIII-12 mentioned hereinabove and obtained from the distillation and molecular distillation can be effectively treated by the GC separation, although the other portions can also be treated.

According to the present invention, hypo-allergic jasmine oil can further be effectively produced by preparative column chromatography. That is, the starting natural jasmine oil is treated with a non-polar solvent such as n-pentane and n-hexane by using a column provided with a polymeric adsorbent or an ion exchange resin. Examples of ion exchange resins are those usable in a nonaqueous solvent system, for example, Amberlyst® A-15, A-21, A-26 and A-27 available from Organo Co. Examples of synthetic adsorbents are styrene-divinylbenzene copolymers such as Amberlite® XAD-2 and XAD-4 available from Organo Co. and acrylate polymers such as Amberlite® XAD-7 and XAD-8 available from Organo Co.

Furthermore, the column chromatography separation can be combined with the above-mentioned distillation and/or molecular distillation methods to produce hypo-allergic jasmine oil. Especially when the above-mentioned MDI-R and MDII-R having a high molecular weight are treated by the column chromatography separation, excellent effects can be obtained. The amounts of the distillates MDI-R and MDII-R are desirably not more than 30 parts by weight. Coniferyl linoleate, coniferyl palmitate and the like present in MDI-R and MDII-R can be simultaneously removed therefrom by the column chromatography separation.

As mentioned thereinabove, hypo-allergenic jasmine oil can be obtained by the various methods according to the present invention. All the jasmine oils obtained from these methods do not contain $U_1$ peak when GPC analysis is carried out under the conditions set forth in Table 5 above and do not contain coniferyl benzoate and coniferyl acetate when MF analysis is carried out under the conditions set forth in Table 12 above. These hypo-allergic jasmine oils obtained from the various methods can be used alone or any mixture thereof for the practical use. The use of the mixture is desirable from the commercial and economical points of view.

Various kinds of treated jasmine oils having no or weak allergenicity and being obtained by removing the allergenic substances from natural jasmine oil can be advantageously used in combination according to the present invention.

For instance, natural jasmine oil is first distilled at the distillation I, thereby separating 32 parts by weight based on 100 parts by weight of the starting jasmine oil of the distillate DI-1 from DI-R. DI-R is then subjected to the molecular distillation I to produce 23 parts by weight of MDI-12 and 15 parts by weight of the second distillate. Twenty-three parts by weight of MDI-12 is subjected to the second distillation II to produce distillate 18 parts by weight of DII-12. DII-12 is then washed with an alkaline solution to produce 16 parts by weight of the alkaline treated portion. Twenty-nine parts by weight of MDI-R derived from the molecular distillation I was subjected to the column chromatography separation to produce 18 parts by weight of the polymeric adsorbent treated portion. Thus, 66 parts by weight (i.e. recovery rate of 66% by weight) of the hypo-allergenic jasmine oil including the distillate DI-1, the alkaline treated portion and the column chromatography treated portion.

The present inventors have furthermore found that unit operations, other than the above-mentioned unit operations alone or in combination therewith, may result in the decrease in the allergic reaction of natural jasmine oil. However, these unit operations are not suitable for use in practical or industrial applications.

In accordance with the present invention, the hypo-allergenic jasmine oil can be compounded with a perfume controlling agent to produce a hypo-allergic jasmine oil composition having extremely excellent odor (or perfume) and having high safety. Examples of such perfume controlling agents are as follows:

(I)

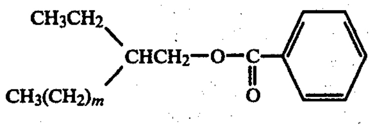

wherein m is 1 or 3.

(II)

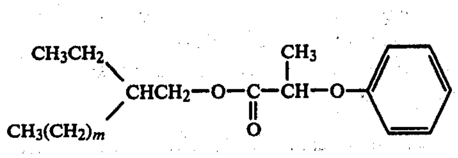

wherein m is 1 or 3.

(III)

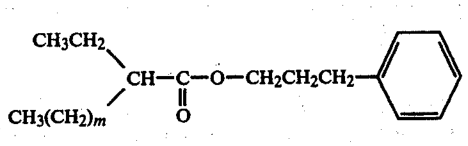

wherein m is 1 or 3.

(IV)

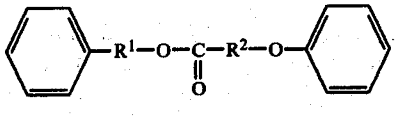

wherein $R^1$ is a saturated linear alkylene group having 1 through 3 carbon atoms and $R^2$ is a saturated linear alkylene group having 1 or 2 carbon atoms.

(V)

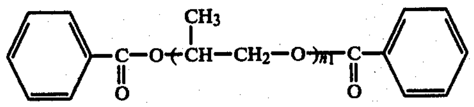

wherein $n_1$ is an integer of 1 through 3.

(VI)

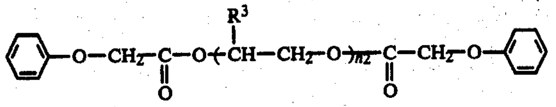

wherein $R^3$ is H, $CH_3$ or $C_2H_5$, $n_2$ is 1 or 2.

(VII)

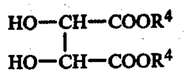

wherein $R^4$ is a saturated branched aliphatic alcohol residue having 6 through 14 carbon atoms.

(VIII)

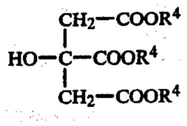

wherein $R^4$ is the same as defined above.

$$R^5OOC(CH_2)_4COOR^6 \quad (IX)$$

wherein $R^5$ and $R^6$ are independently a saturated branched alkyl group having 4 or 5 carbon atoms.

Example of these perfume controlling agents are 2-ethylhexyl benzoate, 2-ethylbutyl benzoate, 2-ethylhexyl-2-phenoxy propionate, 2-ethylbutyl-2-phenoxy propionate, 3-phenylpropyl-2-ethylbutyrate, 3-phenylpropyl-2-ethylhexanoate, 2-phenylethyl phenoxy acetate, 3-phenylpropyl phenoxyacetate, propyleneglycol dibenzoate, dipropyleneglycol diphenoxyacetate, di-2-ethylbutyl tartrate, di-2-ethylhexyl tartrate, tri-2-ethylbutyl citrate, tri-4-methyl-2-pentyl citrate and tri-2-ethylhexyl citrate. These perfume controlling agents can be incorporated into the composition to improve the tenacity, perfume harmonization and stability against an aldehyde. Although there is no critical amount of the perfume controlling agent to be incorporated into the composition, the perfume controlling agent is generally incorporated into the composition in an amount of 40% by weight or less, desirably 5 through 30% by weight.

The present invention now will be further illustrated by, but is by no means limited to, the following Examples, wherein all parts and percentages are expressed on a weight basis, unless otherwise noted.

EXAMPLE 1

A 1,002 g amount of natural jasmine oil (produced in Egypt) were distilled at a first distillation I to obtain 333 g of DI-1 at up to 91° C./0.5 mmHg and 668 g of DI-R. No by-note was observed both in the portions DI-1 and DI-R.

Figure 11:
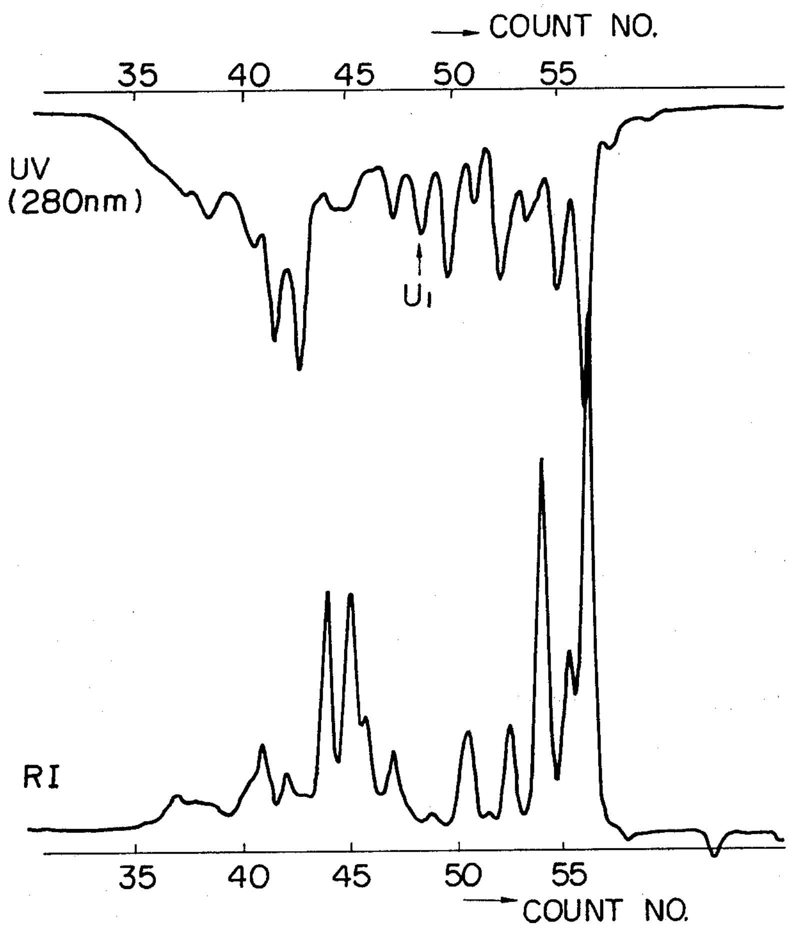
FIG. 11 is a GPC chromatogram of natural jasmine oil (produced in Egypt)

GPC chromatograms of DI-1 and the starting natural jasmine oil are shown in FIGS. 10 and 11, respectively. The analysis was carried out under the conditions set forth in Table 5 above. (GPC analyses in Examples hereinbelow were carried out under the conditions set forth in Table 5 above).

As is clear from the comparison of FIG. 10 with FIG. 11, the chromatogram of the distillate DI-1 has no $U_1$ peak, whereas that of the starting natural jasmine oil has the $U_1$ peak. Furthermore, it was confirmed from a MF analysis that coniferyl acetate and coniferyl benzoate were removed in DI-1.

Allergenicity tests were carried out in the starting natural jasmine oil, DI-1 and DI-R portions. The results are shown in Table 15 below. As is clear from the results shown in Table 15, no allergenicity was observed in the distillate DI-1.

TABLE 15

| Sample | Challenge test concentration (%) | Results |
|---|---|---|
| Natural jasmine oil | 10 | 10/10 (3.2) |
| DI-1 | 3 | 0/10 (0.0) |
| DI-R | 7 | 10/10 (3.1) |

DI-1 was compounded into a perfume composition. Thus, a perfume composition having an excellent perfume was obtained. The formulation was as follows.

| Components | Parts |
|---|---|
| DI-1 of Example 1 | 33.2 |
| Cis-Jasmone | 0.3 |
| Methyl jasmonate | 0.4 |
| Methyl dihydrojasmonate | 4.0 |
| Jasmolactone | 0.2 |
| Indole | 1.0 |

-continued

| Components | Parts |
|---|---|
| Methyl-N—acetyl anthranilate | 0.5 |
| Phytyl acetate | 3.0 |
| Phytyl palmitate | 4.5 |
| Phytyl stearate | 4.5 |
| Geranyl linalool | 3.0 |
| Benzyl benzoate | 6.0 |
| Methyl palmitate | 1.0 |
| squalane | 7.0 |
| Alpha-hexyl cinnamic aldehyde | 2.0 |
| Octadecanol | 0.5 |
| Abs. mimosa | 0.01 |
| Bees wax | 0.1 |
| Abs. son | 0.1 |
| Nonapropylene glycol diglycerine ether | 3.0 |
| 2-ethylhexyl benzoate | 7.0 |
| Di-isobutyl adipate | 7.19 |
| Propylene glycol dibenzoate | 4.0 |
| Glucam P-20 (available from Amerchol) | 7.5 |
| | 100.0 |

EXAMPLE 2

Natural jasmine oil (produced in Egypt) was fractionated under the conditions set forth in Table 16 below by a gas chromatography.

TABLE 16

| | |
|---|---|
| Apparatus | Hitachi Model K-163 GC |
| Column | PEG-20M 20%/Celite 545 DMCS (8 mm i.d. × 2 m, Glass column) |
| Column temp. | 220° C. |
| Injection temp. | 250° C. |
| Detector | FID |
| $N_2$ flow rate | 1.0 kg/cm$^2$, 50 ml/min. |
| $H_2$ flow rate | 1.0 kg/cm$^2$, 40 ml/min. |
| Air flow rate | 1.0 kg/cm$^2$, 500 ml/min. |

A branched tube was provided at the upstream side of the GC detector. One flow path from the branched tube was connected to the detector and the other was connected to a collect tube, which was cooled by a dry ice-methanol bath. Thus, 100 μl of natural jasmine oil was injected into a GC by a syringe and a fraction up to a retention time of 14 min. was separated as a GC separation component. This separation was repeated 40 times. Thus, 2.1 g of a GC separation portion was collected. This portion contained important perfume components such as cis-jasmons, methyl jasmonate, jasmine lactone and the like and had no by-note.

Figure 12:
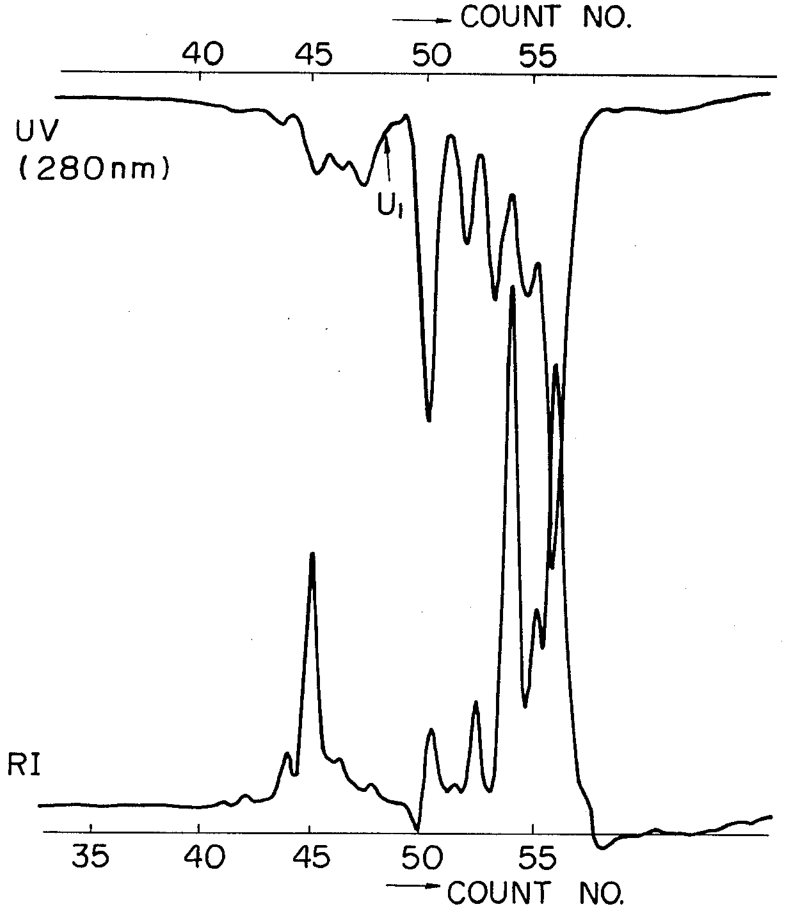
FIG. 12 is a GPC chromatogram of a gas chromatography separation portion of Example 2.

The GPC analysis result of this portion is shown in FIG. 12. As is clear from FIG. 12, the $U_1$ peak disappeared in the GPC chromatogram. Furthermore, as a result of an MF analysis, coniferyl acetate and coniferyl benzoate were not contained in this portion. The allergenicity test of this portion was carried out. The result is shown in Table 17 below. As is clear from the result shown in Table 17, no allergenicity was observed.

TABLE 17

| Sample | Challenge test concentration | Result |
|---|---|---|
| GC separated portion | 5% | 0/10 (0) |

EXAMPLE 3

Ten grams of natural jasmine oil (produced in Egypt) were dissolved in 100 ml of n-hexane. 150 ml of a 3% aqueous sodium hydroxide solution was added to this solution and the mixture was then transferred into a separatory funnel. The funnel was shaked for 15 minutes in a shaking machine and allowed to stand. A n-hexane phase was separated. This n-hexane phase was washed three times with water and, after separation, n-hexane was evaporated under a reduced pressure in an evaporator. Thus, 5.86 g of an alkaline treated portion having no substantial by-note was obtained.

Figure 13:
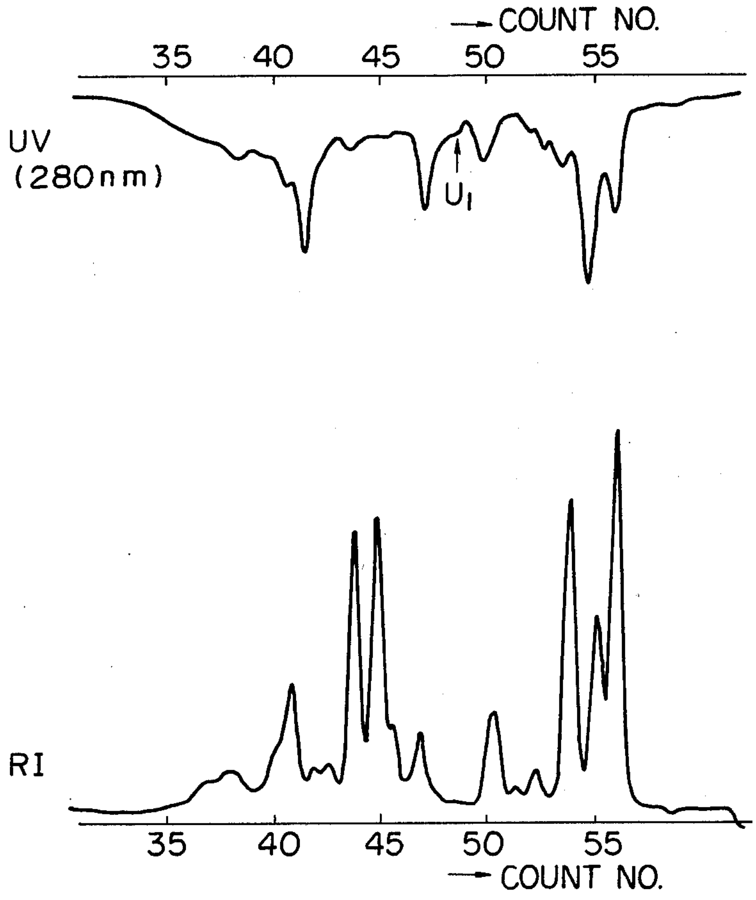
FIG. 13 is a GPC chromatogram of an alkaline treated portion of Example 3.

The GPC analysis result of this portion is shown in FIG. 13. As is clear from FIG. 13, the $U_1$ peak disappeared in this portion. As a result of an MF analysis, coniferyl acetate and coniferyl benzoate are not contained in this portion.

The allergenicity test of this portion was carried out and it was confirmed that the allergenicity of the alkaline treated portion was weak. The result is shown in Table 18 below.

TABLE 18

| Sample | Challenge test concentration | Result |
|---|---|---|
| Alkaline treated portion | 6% | 5/10 (0.5) |

EXAMPLE 4

One thousand grams of natural jasmine oil (produced in Egypt) were distilled at a first distillation I to obtain 102 g of a portion DI-1 having a distillation temperature of up to 62° C./0.4 mmHg and 897 g of DI-R. There was no by-note both in the portions DI-1 and DI-R. The portion DI-1 had no allergenicity.

Eight hundred and eighty grams of the portion DI-R were subjected to molecular distillation I by using a centrifugal type molecular distillation apparatus CMS-5A (available from Bendix Co). Thus, 148 g of a portion MDI-1 having a distillation temperature of up to 60° C./8.4–11.1$\times 10^{-2}$ mmHg and 731 g of MDI-R were obtained. There was no by-note in the portions MDI-1 and MDI-R. The GPC analysis showed that no $U_1$ peak was present in the portions DI-1 and MDI-1. Furthermore the MF analysis showed that coniferyl acetate and coniferyl benzoate were not present in the portions DI-1 and MDI-1. No allergenicity was observed in the portions DI-1 and MDI-1 according to the allergenicity test. The results are shown in Table 19 below.

TABLE 19

| Sample | Challenge test concentration | Results |
|---|---|---|
| DI-1 | 1% | 0/10 (0) |
| MDI-1 | 2% | 0/10 (0) |

EXAMPLE 5

Twenty grams of the portion DI-R obtained in Example 1 were treated in a column chromatography provided with 300 ml of a synthetic adsorbent, Amberlite®XAD-7. The adsorbent was thoroughly washed with water and dried to remove the foreign odor from the polymeric adsorbent before the filling thereof into the column. Twenty grams of DI-R were developed by using 1 liter of n-pentane as a developing liquid. The effluent was collected and n-pentane was evaporated under a reduced pressure in an evaporator. Thus, 14.2 g of a synthetic adsorbent treated portion having no substantial by-note was obtained.

The GPC analysis showed that $U_1$ peak disappeared in the chromatogram of this portion. Furthermore, the MF analysis showed that coniferyl acetate and coniferyl benzoate were not present in the adsorbent treated portion. The result of the allergenicity test is shown in Table 20 below. As is clear from the result shown in Table 20, no allergenicity was observed in the adsorbent treated portion.

TABLE 20

| Sample | Challenge test concentration | Result |
|---|---|---|
| Adsorbent treated portion | 5% | 0/10 (0) |

EXAMPLE 6

One thousand grams of natural jasmine oil (produced in Egypt) were distilled at a first distillation I to obtain 102 g of DI-1 having a distillation temperature of up to 61° C./0.5 mmHg and 896 g of DI-R. Eight hundred and fifty grams of DI-R was subjected to a molecular distillation I by using a molecular distillation apparatus model CMS-5A available from Bendix Co. Thus, the following three fractions were obtained.

MDI-1: 65 g, −58° C./8.3−12.4$\times 10^{-2}$ mmHg

MDI-2: 472 g, 58°-110° C./2.6−8.3$\times 10^{-2}$ mmHg

MDI-R: 312 g,

Fifty grams of MDI-2 was distilled at a second distillation II to obtain 24 g of DII-1 having a distillation temperature of up to 118° C./0.4 mmHg and 25 g of DII-R.

The GPC analysis showed that there is no $U_1$ peak in the portions DI-1, MDI-1 and DII-1. Furthermore, the MF analysis showed that coniferyl acetate and coniferyl benzoate are not present in these portions. As is clear from the allergenicity test results shown in Table 21 below, no allergenicity was observed in the portions DI-1, MDI-1 and DII-1.

TABLE 21

| Sample | Challenge test concentration | Result |
|---|---|---|
| DI-1 | 1% | 0/10 (0) |
| MDI-1 | 1% | 0/10 (0) |
| DII-1 | 2% | 0/10 (0) |

EXAMPLE 7

Five hundred grams of natural jasmine oil (produced in Egypt) were distilled at a first distillation I to obtain 51 g of DI-1 having a distillation temperature of up to 60° C./0.4 mmHg and 447 g of DI-R. 400 g of DI-R was subjected to a molecular distillation step I by using the same apparatus used in Example 4. Thus, 240 g of MDI-12 having a distillation temperature of up to 108° C./2.6-12.5$\times 10^{-2}$ mmHg and 138 g of MDI-R were obtained. 50.0 g of MDI-12 thus obtained was then distilled at a second distillation II. Thus, 23.4 g of DII-1 having a distillation temperature of up to 128° C./0.5 mmHg and 26.2 g of DII-R.

There was no by-note was observed in the portions DI-1, DI-R, MDI-12, MD-R, DII-1 and DII-R. The GPC analysis showed that there was no $U_1$ peak in the portions DI-1 and DII-1. The MF analysis showed that coniferyl acetate and coniferyl benzoate were not present in DI-1 and DII-1. As is clear from the allergenicity test results shown in Table 22 below, no allergenicity was observed in the portions DI-1 and DII-1.

TABLE 22

| Sample | Challenge test concentration | Result |
|---|---|---|
| DI-1 | 1% | 0/10 (0) |
| DII-1 | 2% | 0/10 (0) |

EXAMPLE 8

Six hundred grams of DI-R obtained in Example 1 were subjected to a molecular distillation I by using the same molecular distillation apparatus as in Example 4. Thus, 313 g of MDI-12 having a distillation temperature of up to 110° C./2.6−8.9$\times 10^{-2}$ mmHg and 285 g of MDI-R. 20.0 g of MDI-12 thus obtained was subjected to a column chromatography treatment in the same manner as described in Example 5. Thus, 18.0 g of a polymeric adsorbent treated portion was obtained.

There was no substantial by-note in the portions MDI-12 and MDI-R as well as the adsorbent treated portion. The GPC analysis showed that the $U_1$ peak disappeared in the adsorbent treated portion. The MF analysis showed that coniferyl acetate and coniferyl benzoate were not present in the adsorbent treated portion. As is clear from the allergenicity test result shown in Table 23 below, it was confirmed that the allergenicity of the adsorbent treated portion was weak.

TABLE 23

| Sample | Challenge test concentration | Result |
|---|---|---|
| MDI-12 | 3% | 10/10 (2.8) |
| Adsorbent treated portion | 3% | 3/10 (0.3) |

EXAMPLE 9

The portion MDI-12 of Example 8 was subjected to a GC separation in the same manner as described in Example 2. Thus, 1.1 g of a GC separation treated portion was obtained.

There was no by-note in this portion. The GPC analysis showed that no $U_1$ peak was present in this portion. The MF analysis showed that coniferyl acetate and coniferyl benzoate were not present in this portion.

As is clear from the allergenicity test result shown in Table 24 below, it was confirmed that this portion had no allergenicity.

TABLE 24

| Sample | Challenge test concentration | Result |
|---|---|---|
| GC treated portion | 1% | 0/10 (0) |

EXAMPLE 10

Ten grams of the MDI-12 portion of Example 8 were dissolved in 100 ml of n-hexane and 100 ml of an aqueous 1% sodium hydroxide solution was then added thereto. This mixture was charged into a 500 ml separatory funnel. The separatory funnel was shaked for 20 minutes in a skaking machine. Then, the shaked mixture was separated by means of a centrifugal separator to separate the mixture into two phases. n-Hexane phase was collected and washed with water three times. n-Hexane was evaporated under a reduced pressure in an evaporator to recover 7.1 g of the alkaline treated portion.

This alkaline treated portion contained reduced amounts of important perfume components such as jasmine lactone, but had no by-note. The GPC analysis showed that no $U_1$ peak was present in this portion. The MF analysis showed that coniferyl acetate and coniferyl benzoate were not contained in this portion. As is clear from the allergenicity test result shown in Table 25 below, no allergenicity was observed in the alkaline treated portion.

TABLE 25

| Sample | Challenge test concentration | Result |
|---|---|---|
| Alkaline treated portion | 4% | 0/10 (0) |

EXAMPLE 11

Twenty grams of MDI-R of Example 8 were subjected to a column chromatography treatment by using Amberlite ®XAD-7 as the synthetic adsorbent in the same manner as described in Example 5. Thus, 13.0 g of a synthetic adsorbent treated portion was obtained.

Figure 14:
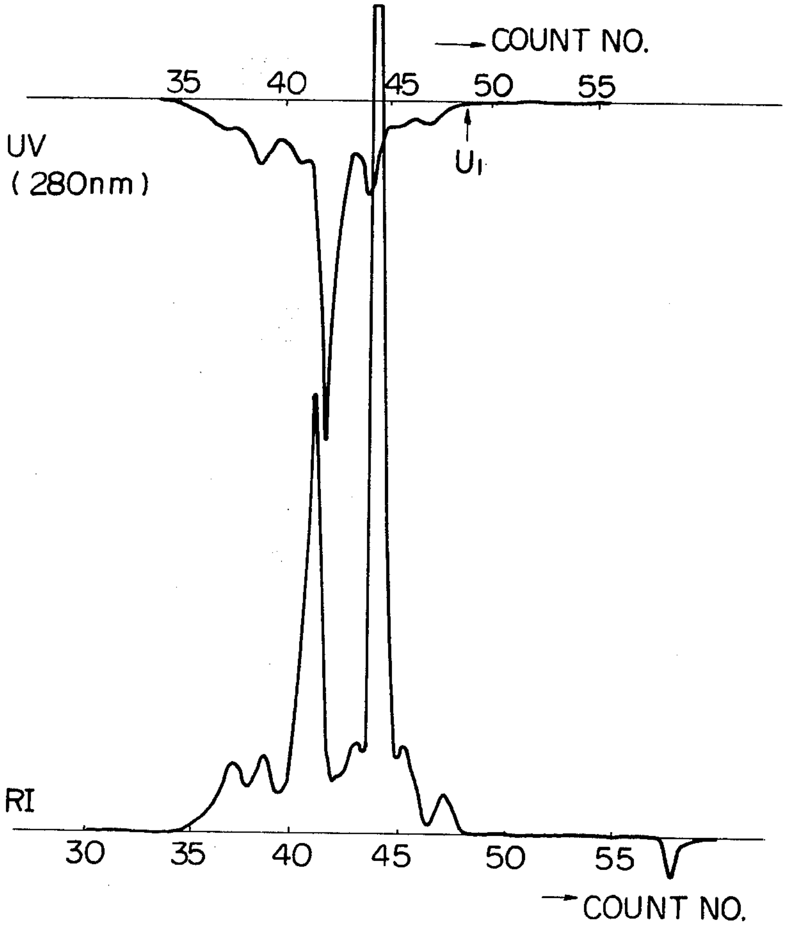
FIG. 14 is a GPC chromatogram of a synthetic adsorbent treated portion of MDI-R portion of Example 14.

There was no by-note in this portion. As is clear from the GPC analysis result of this portion shown in FIG. 14, the $U_1$ peak disappeared in this portion. Furthermore, the MF analysis showed that coniferyl acetate and coniferyl benzoate were not contained in this portion. As is clear from the allergenicity test results shown in Table 26 below, no allergenicity was observed in the adsorbent treated portion.

TABLE 26

| Sample | Challenge test concentration | Result |
|---|---|---|
| MDI-R | 3% | 10/10 (2.8) |
| Adsorbent treated portion | 2% | 0/10 (0) |

EXAMPLE 12

Five hundred grams of natural jasmine oil (produced in Egypt) was distilled at a first distillation I to obtain 158 g of DI-1 having a distillation temperature of up to 93° C./0.5 mmHg and 340 g of a residue DI-R.

Three hundred and thirty grams of DI-R were subjected to a molecular distillation I by using the same molecular distillation apparatus as used in Example 4. Thus, 114 g of MDI-12 having a distillation temperature of up to 81° C./3.1–$6.0\times10^{-2}$ mmHg, 73 g of a second distillate having a distillation temperature of 81°–109° C./2.6–$3.1\times10^{-2}$ mmHg and 141 g of MDI-R were obtained. 30.0 g of the portion MDI-12 was distilled at a distillation II to obtain 22.6 g of DII-12 having a distillation temperature of up to 130° C./0.5 mmHg and 6.9 g of DII-R. 5.0 g of DII-12 thus obtained was diluted with 10 ml of n-hexane and, then, mixed with 10 ml of a 0.02N aqueous potassium hydroxide solution. The resultant mixture was thoroughly shaked and separated into a n-hexane phase and an aqueous phase. The n-hexane phase was collected and, after washing with water, n-hexane was evaporated under a reduced pressure in an evaporator. Thus, 4.5 g of an alkaline treated portion was obtained.

Furthermore, 20.0 g of the residue MDI-R was subjected to a column chromatography treatment in the same manner as described in Example 5. Thus, 12.4 g of an adsorbent treated portion was obtained.

There was no substantial by-note in the alkaline treated portion. The GPC analysis showed that the $U_1$ peak disappeared in this portion and the MF analysis showed that coniferyl acetate and coniferyl benzoate were not contained in this portion. As is clear from the allergenicity test results shown in Table 27 below, it was confirmed that the allergenicity of the alkaline treated portion was weak.

TABLE 27

| Sample | Challenge test concentration | Results |
|---|---|---|
| DII-12 | 2% | 10/10 (1.1) |
| Alkaline treated portion | 2% | 2/10 (0.2) |

The portion DI-1, the alkaline treated portion and the adsorbent treated portion were compounded into a perfume composition. Thus, a perfume composition having an excellent perfume was obtained. The formulation was as follows.

| Components | Parts |
|---|---|
| DI-I of Example 12 | 31.0 |
| Alkaline treated portion of Example 12 | 15.2 |
| Adsorbent treated portion of Example 12 | 18.0 |
| Methyl dihydrojasmonate | 3.0 |
| Cis-jasmone | 1.0 |
| Alpha-hexyl cinnamic aldehyde | 1.0 |
| Diisobutyl adipate | 5.0 |
| Propylene glycol dibenzoate | 8.49 |
| Trimethylol propane triisostearate | 8.0 |
| Glucam P20 (available from Amerchol) | 9.0 |
| Abs. mimosa | 0.01 |
| Bees wax | 0.2 |
| Abs. son | 0.1 |
| | 100.0 |

EXAMPLE 13

One thousand grams of natural jasmine oil (produced in Morocco) were subjected to a molecular distillation II by means of the same molecular distillation apparatus as used in Example 6. Thus, 221 g of MDII-1 having a distillation temperature of up to 60° C./8.0–$12.5\times10^{-2}$ mmHg, 475 g of MDII-2 having a distillation temperature of 60°–110° C./2.6–$8.0\times10^{-2}$ mmHg and 303 g of MDII-R. 230 g of MDII-2 was distilled at a distillation III, thereby obtaining 72 g of DIII-1 having a distillation temperature of up to 125° C./0.5 mmHg and 156 g of DIII-R.

There was no by-note in the portions MDII-1, MDII-2, MDII-R, DIII-1 and DIII-R. The GPC analysis of MDII-1 and DIII-1 showed that no $U_1$ peak was present in these portions. Furthermore, the MF analysis of these portions showed that coniferyl benzoate and coniferyl acetate were not contained. As is clear from the allergenicity test results shown in Table 28 below, allergenicity was not observed in the portions MDII-1 and DIII-1.

TABLE 28

| Sample | Challenge test concentration (%) | Result |
|---|---|---|
| Natural jasmine Oil | 10 | 10/10 (3.4) |
| MDII-1 | 2 | 0/10 (0) |
| DIII-1 | 1 | 0/10 (0) |

EXAMPLE 14

Twenty grams of the portion MDII-2 of Example 13 were subjected to a column chromatography treatment in the same manner as used in Example 5 by using Amberlite ®XAD-8 as the synthetic adsorbent. Thus, 16.4 g of the adsorbent treated portion was obtained.

There was no by-note in this portion. The GPC analysis of this portion showed that no $U_1$ peak was present. Furthermore, the MF analysis of this portion showed that coniferyl acetate and coniferyl benzoate were not contained. As is clear from the allergenicity test results shown in Table 29 below, the allergenicity of the adsorbent treated portion was decreased.

TABLE 29

| Sample | Challenge test concentration (%) | Result |
|---|---|---|
| MDII-2 | 5 | 10/10 (2.7) |
| Adsorbent treated portion | 4 | 4/10 (0.4) |

EXAMPLE 15

MDII-2 of Example 13 was subjected to a gas chromatography separation under the same conditions as in Example 2. Thus, 1.5 g of a GC treated portion was obtained.

There was no by-note in this GC treated portion. The GPC analysis of this portion showed that no $U_1$ peak was observed. Furthermore, the MF analysis of this portion showed that coniferyl acetate and coniferyl benzoate were not contained in this portion. As is clear from the allergenicity test result shown in Table 30 below, no allergenicity was observed in this portion.

TABLE 30

| Sample | Challenge test concentration | Result |
|---|---|---|
| GC treated portion | 1% | 0/10 (0) |

EXAMPLE 16

Ten grams of MDII-2 obtained in Example 13 were subjected to an alkaline treatment under the same conditions as in Example 3. Thus, 8.5 g of the alkaline treated portion was obtained.

There was no by-note in this portion. The GPC analysis of this portion showed that no $U_1$ peak was present. Furthermore, the MF analysis showed that coniferyl acetate and coniferyl benzoate were not contained in this portion. As is clear from the allergenicity test result shown in Table 31 below, no allergenicity was observed in this portion.

TABLE 31

| Sample | Challenge test concentration | Result |
|---|---|---|
| Alkaline treated portion | 4% | 0/10 (0) |

EXAMPLE 17

One hundred and fifty grams of MDII-2 of Example 13 was subjected to a distillation III. Thus, 77 g of DIII-12 having a distillation temperature of up to 130° C./0.4 mmHg and 71 g of DIII were obtained. 30 g of DIII-12 was diluted with 60 ml of n-hexane and 90 ml of a 0.02N aqueous potassium hydroxide solution was mixed therewith. The mixture was thoroughly shaken and separated. The n-hexane phase thus separated was collected and washed three times with water. Thereafter, n-hexane was evaporated under a reduced pressure in an evaporator. Thus, 29 g of the alkaline treated portion was obtained.

There was no by-note in this alkaline treated portion. The GPC analysis of this portion showed that no $U_1$ peak was present. The MF analysis of this portion showed that coniferyl acetate and coniferyl benzoate were not contained. As is clear from the allergenicity test results shown in Table 32 below, the allergenicity of the alkaline treated portion was weak.

TABLE 32

| Sample | Challenge test concentration | Results |
|---|---|---|
| DIII-12 | 3% | 9/10 (1.2) |
| Alkaline treated portion | 3% | 2/10 (0.2) |

EXAMPLE 18

Twenty grams of MDII-R of Example 13 was subjected to a column chromatography treatment under the same conditions as in Example 5. Thus, 13.2 g of a synthetic adsorbent treated portion was obtained.

There was no by-note in this portion. The GPC analysis of this portion showed that no $U_1$ peak was present. Furthermore, the MF analysis showed that coniferyl acetate and coniferyl benzoate were not contained in this portion. As is clear from the allergenicity test results shown in Table 33 below, no allergenicity was observed in the adsorbent treated portion.

TABLE 33

| Sample | Challenge test concentration | Results |
|---|---|---|
| MDII-R | 3% | 10/10 (2.6) |
| Adsorbent treated portion | 2% | 0/10 (0) |

EXAMPLE 19

One thousand grams of natural jasmine oil (produced in Italy) were subjected to a molecular distillation II by means of a molecular distillation apparatus Model CMS-5A available from Bendix Co. Thus, 558 g of MDII-12 having a distillation temperature of up to 85° C./4.0–13.2×$10^{-2}$ mmHg and 441 g of MDII-R. 500 g of MDII-12 was subjected to a distillation III, whereby 313 g of DIII-1 having a distillation temperature of up to 92° C./0.4 mmHg, 99 g of DIII-2 having a distillation temperature of 92°–128° C./0.4 mmHg and 86 g of DIII-R were obtained. 60 g of DIII-2 was diluted with 120 ml of n-hexane and 150 ml of a 0.02N aqueous potassium hydroxide solution was then mixed. The mixture was thoroughly shaked and separated. The n-hexane phase was washed with water three times and, then, n-hexane was evaporated under a reduced pressure in an evaporator. Thus, 56 g of the alkaline treated portion was obtained. 20.0 g of MDII-R was subjected to a column chromatography separation treatment under the same conditions as in Example 5, whereby 14.1 g of the synthetic adsorbent treated portion was obtained.

There was no by-note in the portions MDII-12, MDII-R, DIII-1, DIII-2, DIII-R, the alkaline treated portion and the adsorbent treated portion. The GPC analysis of DIII-1, the alkaline treated portion and the adsorbent treated portion showed that no $U_1$ peak was present. Furthermore, the MF analysis of these portions showed that coniferyl acetate and coniferyl benzoate were not contained. The allergenicity tests of the above-mentioned seven portions as well as the starting natural jasmine oil were carried out. The results are shown in Table 34 below. As is clear from the results shown in Table 34 below, it was confirmed that the allergenicity of DIII-1, the alkaline treated portion and the adsorbent treated portion was weak.

TABLE 34

| Sample | Challenge test concentration | Results |
|---|---|---|
| Natural jasmine oil (Italy) | 10% | 10/10 (3.3) |
| MDII-12 | 6% | 10/10 (2.1) |
| DIII-1 | 3% | 1/10 (0.1) |
| DIII-2 | 2% | 9/10 (1.3) |
| Alkaline treated portion | 2% | 4/10 (0.4) |
| MDII-R | 4% | 10/10 (2.7) |
| Adsorbent | 3% | 1/10 (0.1) |

The portion DIII-1, the alkaline treated portion and the adsorbent treated portion were compounded into a perfume composition. Thus, a perfume composition having an excellent perfume was obtained. The formulation was as follows.

| Components | Parts |
|---|---|
| DIII-1 of Example 19 | 35.0 |
| Alkaline treated portion of Example 19 | 6.5 |
| Adsorbent treated portion of Example 19 | 29.8 |
| Cis-jasmone | 0.3 |
| Methyl jasmonate | 0.4 |
| Methyl dihydrojasmonate | 2.5 |
| Jasmolactone | 0.3 |
| Indole | 1.0 |
| Methyl-N—acetyl anthranilate | 0.5 |
| Phytyl acetate | 3.0 |
| Phytyl palmitate | 2.0 |
| Phytyl stearate | 2.0 |

-continued

| Components | Parts |
|---|---|
| Geranyl linalool | 3.0 |
| Benzyl benzoate | 6.0 |
| Methyl palmitate | 1.0 |
| Cis-3-hexenyl benzoate | 0.1 |
| Eugenol | 0.5 |
| Abs. mimosa | 0.01 |
| Bees wax | 0.1 |
| Abs. son | 0.1 |
| Alpha-hexyl cinnamic aldehyde | 1.2 |
| Diisobutyl adipate | 2.5 |
| Propylene glycol dibenzoate | 2.19 |
| | 100.0 |

We claim:

1. Hypo-allergenic jasmine oil from which coniferyl benzoate and coniferyl acetate are removed.

2. Hypo-allergenic jasmine oil in which substances having a count number of 47.5 through 49.5 determined by gel permeation chromatography in four TSKGEL G 2000 H8 columns in series under the conditions defined below are removed, Temperature: 40° C., Solvent: Tetrahydrofuran (THF), Flow Rate: 1.0 ml/min at 80 kg/cm$^2$, Sample amount: 100 ul of 0.2 through 2% by weight sample solution in THF, Wavelength: 280 nm.

3. A process for producing hypo-allergenic jasmine oil in which coniferyl benzoate and coniferyl acetate are removed from natural flower essential jasmine oil comprising subjecting such jasmine oil to at least one of distillation, molecular distillation, preparative gas chromatography, and preparative column chromatography, alkaline treatment or any combination thereof.

4. A hypo allergenic jasmine composition comprising (i) hypo allergenic jasmine oil in which coniferyl benzoate and coniferyl acetate are substantially removed and (ii) a perfume controlling agent.

* * * * *

UNITED STATES PATENT AND TRADEMARK OFFICE

CERTIFICATE OF CORRECTION

PATENT NO. : 4,464,290

DATED : August 7, 1984

INVENTOR(S) : Saburo Ohta et al

It is certified that error appears in the above-identified patent and that said Letters Patent is hereby corrected as shown below:

| | |
|---|---|
| Col. 2, line 12 | Delete "quinea" and substitute --guinea-- |
| Col. 4, line 52 | Table 3, second column, 3rd line, delete "kiki" and substitute --Kiki-- |
| Col. 7, line 8 | Delete "Protan"and substitute --Proton- |
| Col. 8, line 50 and Col. 12, line 68 | After "hypo-" delete "allergic" and substitute --allergenic-- |
| Col. 15, line 46 | Delete "jasmons" and substitute --jasmone-- |
| Col. 24, line 35 | After "treatment" delete "or any combination thereof" |
| Col. 24, line 38 | Before "removed" delete "substantially" |

Signed and Sealed this

*Twelfth* Day of *February 1985*

[SEAL]

*Attest:*

DONALD J. QUIGG

*Attesting Officer* *Acting Commissioner of Patents and Trademarks*